United States Patent [19]
Kanetaka et al.

[11] 4,035,353
[45] July 12, 1977

[54] PROCESS FOR PRODUCING HEXAMETHYLENEIMINE

[75] Inventors: Junichi Kanetaka; Takashi Shimodaira; Nobuhiko Fuga; Kuniaki Hayasi; Tadashi Ayusawa, all of Amimachi, Japan

[73] Assignee: Mitsubishi Petrochemical Company Limited, Japan

[21] Appl. No.: 533,536

[22] Filed: Dec. 17, 1974

[30] Foreign Application Priority Data

Dec. 18, 1973 Japan ............................ 48-141456
Dec. 18, 1973 Japan ............................ 48-141457

[51] Int. Cl.$^2$ ..................................... C07D 295/02
[52] U.S. Cl. ........................... 260/239 B; 252/470
[58] Field of Search ................................. 260/239 B

[56] References Cited

U.S. PATENT DOCUMENTS 2,181,140  11/1939  Lazier ........................ 260/239.3 A
2,772,291  11/1956  McShane, Jr. .................. 260/343.6

FOREIGN PATENT DOCUMENTS 1,320,839  6/1973  United Kingdom
763,666    12/1955  United Kingdom

OTHER PUBLICATIONS

House, Modern Synthetic Rreactions, 2nd Ed., 1972, p. 9.
McAlees et al., J. Chem. Soc. 1969, p. 2425.
R. L. Augustine, "Catalytic Hydrogenation", pp. 89–90, Marcel Dekker, Inc. N. Y. (1965).
Freifelder et al., "Practical Catalytic Hydrogenation", pp. 498–507, 543, Wiley Interscience.
Kanetaka, Chem. Labs. 82, 139415a (1974).
Kanetaka, Chem. Abs. 83, 131491x (1975).
Rylander, "Catalytic Hydrogenation over Platinum Metals", pp. 309–310, 320, Academic Press, Inc., N.Y. 1967.
Lanchec et al., "Bull. de la Soc. Chim. de France, p. 3981, 1966.

Primary Examiner—Raymond V. Rush
Assistant Examiner—Mark L. Berch
Attorney, Agent, or Firm—Robert E. Burns; Emmanuel J. Lobato; Bruce L. Adams

[57] ABSTRACT

Process for producing hexamethyleneimine by catalytic hydrogenation of $\epsilon$-caprolactam in a liquid phase which comprises contacting $\epsilon$-caprolactam with hydrogen over a catalyst selected from the group consisting of:
   a. essentially cobalt-molybdenum catalysts, and
   b. essentially cobalt-rhenium-molybdenum catalysts.

12 Claims, No Drawings

PROCESS FOR PRODUCING HEXAMETHYLENEIMINE

BACKGROUND OF THE INVENTION

The present invention relates to a process for producing hexamethyleneimine by catalytic hydrogenation of ε-caprolactam.

Hexamethyleneimine is a useful compounds as a physiologically active substance, particularly as an intermediate material for agricultural chemicals.

As processes for producing hexamethyleneimine, there have been heretofore proposed a process comprising reducing ε-caprolactam with a metal hydride such as LiAlH$_4$ or HaBH$_4$ (for example, Hel.chim.Acta. 32, 544(49). Tetrehedron Letters 1968 (1) 61. ) and a process comprising deammonizing hexamethylenediamine (for example, see, Ber. 96,924(1963), J. Chem. Soc. Japan, Pure Chem. Sec. 82, 1700 (1961) ). However, these known methods are accompanied by various problems such as low yield and high cost of starting materials, and therefore they are not suitable for industrial purposes.

The reaction process for producing a cyclic amine by a catalytic hydrogenation of a cyclic amide tends to cause a side reaction such as a ring cleavage reaction which makes it difficult to obtain the cyclic amine in a good yield. In addition, this process entails a great number of problems which must be solved, such as a remarkable reduction in reaction rate due to the formation of polyamides due to the polymerization of the cyclic amide and a reduction in the activity of the catalyst due to the poison action of the amino acid formed.

It is known that a copper-chromium catalyst [for example, Homer Adkins. J.A.C.S. 56, 2419 (1934) ] and a rhenium catalyst [for example, H.-Smith Broadbent, J.O.C. 24, 1847 (1959) ] are excellent catalysts for the production of an amine by catalytic hydrogenation of an amide. However, when the catalytic hydrogenation is carried out with the use of these catalysts, for example, the copper-chromium catalyst, the reaction must be carrid out at a temperature of 200° to 300° C and at a pressure of 200 to 300 kg/cm$^2$G in the presence of a large quantity amounting to 10 to 20% or more of the catalyst. The use of such a large quantity of the catalyst under a high pressure is considered to be necessary because the reaction must be completed as rapidly as possible since the water formed decomposes the amide into an acid which poisons the catalyst. On the other hand, in the case of the use of the latter rhenium catalyst, the reaction is carried out at a temperature of 150° to 250° C and at a high pressure of 200 to 300 kg/cm$^2$G, although the catalyst is used in a quantity of 1 to 2%, based on the amount of the material to be reacted.

Also, a method for producing hexamethyleneimine by reduction of ε-Caprolactam in the presence of a catalyst for hydrogenation has been proposed (U.S. Pat. No. 2181140). In this method, the catalyst used comprises a single member selected from the group consisting of nickel and cobalt of the VIII Group elements and copper of the IB Group and zinc and cadmium of the II Group B elements, respectively, in the periodic table, or a combination of these elements. However, the reduction reaction is also carried out at a pressure as high as 200 atmospheres. Although the specification of this patent does not disclose the conversion of the ε-caprolactam and the yield of the hexamethyleneimine in detail, it may not ne considered that this method can overcome the afore-mentioned difficulties such as the activity reduction due to catalyst poisoning.

In fact, when we carried out the catalytic hydrogenation of the ε-caprolactam with the use of the known catalyst mentioned above, it was expectedly found that the catalyst was of low activity and of no use for industrial purposes. Therefore, there is a need for a novel catalyst for this technique.

SUMMARY OF THE INVENTION

It is an object of the present invention to overcome the above described difficulties and to provide a process for carrying out catalytic hydrogenation of ε-caprolactam efficiently. The above object can be achieved by the use of a catalyst for hydrogenation having a good acid resistance and/or the adoption of a specific mode of hydrogenation.

The process for producing hexamethyleneimine according to the present invention which comprises catalytically hydrogenating ε-caprolactam is characterized by the use of a catalyst selected from the group consisting of a). essentially cobalt-molybdenum catalysts, and b). essentially cobalt-rhenium-molybdenum catalysts.

Further, in a preferred embodiment of the process of the present invention, the hydrogenation reaction is carried out in the presence of a specific solvent, that is, a straight chain or cyclic saturated hydrocarbon having from 9 to 14 carbon atoms, dioxane, or diethyleneglycol dialkyl ether, and the starting ε-caprolactam, is charged in a liquid phase into a liquid phase of a catalytic reaction zone maintained at a substantially constant temperature, the reaction product being removed in a gas phase together with any excess of hydrogen gas from the reaction zone.

In this manner, the present invention has solved the aforementioned problems due to the acidification of the reaction zone accompanying the progress of the catalytic hydrogenation or to the decomposition of the product by the use of a specific acid-resistant catalyst and, optionally, a specific solvent or by the adoption of a specific mode of hydrogenation. The use of the acid-resistant catalyst makes possible a hydrogenation operation for a long period of time under the condition of a lower pressure or a smaller quantity of the catalyst used than in the case when known catalysts are used. In addition, the adoption of the specific operational mode of hydrogenation facilitates the control of the reaction temperature and, further, makes possible suppression of the secondary reaction of the hexamethyleneimine produced to a minimum.

DETAILED DESCRIPTION

1. CATALYST

The catalyst used in the process of the present invention is selected from the following catalysts, essentially-molybdenum catalysts, and cobalt-molybdenum catalysts, essentially cobalt-rhenium-molybdenum catalysts.

In these catalysts, the cobalt, rhenium, and molybdenum are preferably intimately combined with each other, that is, in a form which can be said to be an intimate composite of these components.

In view of the fact, which will be disclosed hereinbelow, that cobalt is the predominent components in thse multicomponent catalysts, these catalysts are basically cobalt catalysts, or are modified cobalt catalysts. The modifiers rhenium and molybdenum are believed to improve the basic cobalt catalysts in that activities of these basic catalysts are improved and that lives of these basic catalysts are prolonged due to improvement in stability against acids which may be produced by hydration of ε-caprolactam during the hydrogenation and may come to contact with the catalyst. The modifier molybdenum, when used together with rhenium, may support the contribution of rhenium.

Among the six groups of catalysts set forth above, the especially preferred catalysts are the cobalt-rhenium-molybdenum catalysts, cobalt-molybdenum catalysts.

The catalyst of the present invention may be prepared by various methods. It may or not be carried on a support or carrier. However, it is preferred that the catalyst be prepared in the form of a supported catalyst by the following method.

A compound capable of decomposing to metallic cobalt or a metal composed of cobalt on heating in a reducing atmosphere, a rhenium compound capable of decomposing to metallic rhenium on heating in a reducing atmosphere, and a molybdenum compound capable of decomposing to metallic molybdenum on heating in a reducing atmosphere are selected in an appropriate combination, and the selecred compounds are intimately combined on a carrier. The resulting aggregate is heated in a reducing atmosphere until these compounds decompose to form a cobalt-molybdenum, nickely-cobalt-molybdenum, or cobalt-rhenium-molybdenum alloy.

The above described preparation method may be carried out by various methods. In order to intimately combine two to four kinds of the compounds, a method comprising a solution immersion procedure is preferably used. More specifically, the compounds to be combined per se or the precursors or the derivatives are preferably introduced into a support in the form of a solution, particularly an aqueous solution. In this case, a method comprising immersing a support with the respective solutions of the two to four compounds or a mixture solution thereof, a method comprising simultaneously precipitating these compounds onto a support from a solution by means of a precipitation reagent, or a method comprising first precipitating either one to three of the two to four compounds onto a support and subsequently impregnating the resulting support with the remaining compound may be utilized.

More specifically, a method comprising immersing a support with a cobalt compound or a rhenium compound or their mixtures and a molybdenum compound from an aqueous solution containing these compounds dissolved therein, a method comprising depositing cobalt onto a support by dropwisely adding a precipitation reagent to an aqueous solution of a cobalt compound containing a support dispersed therein, drying the supported metal salts and immersing the dried aggregate with an aqueous solution of a soluble rhenium compound and/or a soluble molybdenum compound, or a method comprising uniformly kneading a rhenium compound and/or a molybdenum compound in the form of an aqueous solution into a cobalt salt cake resulting from a cobalt compound by the addition of a precipitation reagent and depositing the resulting compound component onto a support by a kneading means may be practiced.

Examples of the cobalt compounds are nitrates, sulfates, chlorides, and various salts of organic acids, Examples of the precipitation reagent are ammonium carbonate, ammonium bicarbonate, sodium carbonate, and sodium hydroxide. Examples of the rhenium compound are rhenium heptoxide and ammonium perrhenate. Examples of the molybdenum compound are molybdic acid and ammonium molybdate. In the case where a support is used, it is preferably a support conventionally known as a porous support. Such a support may include silica, alumina, diatomaceous earth, silica-alumina, active carbon, magnesia, zirconia, barium carbonate, and the like. However, these supports are not necessarily equal in their initial activity, effective life for a prolonged sevice and the like. In particular, zirconia or silica-alumina seems to be useful for long service.

The supported mixture of the cobalt compound and/or the rhenium compound and the molybdenum compound produced according to the above described process is well dried at a temperature of 80° to 120° C, and the dried mixture is reduced in a reducing atmosphere at a temperature of 300° to 800° C, preferably 350° to 600°C, for a few hours or more to obtain a catalyst. Further, it is possible to introduce a step of decomposing these metal compounds in air or a nitrogen stream prior to the reduction step.

In any appropriate step among the above-mentioned steps, a suitable binder may be added, if desired, to the catalyst component to form a catalyst having a suitable shape.

Because the catalyst thus produced is inflammable on rapid contact with air, the catalyst may be treated with air dilated with carbon dioxide or inert gases to render its handling convenient. In use, the catalyst thus stabilized is ordinally pre-reduced in an atmosphere of hydrogen gas at a temperature of 100° to 200° C.

With respect to each metal component of the novel catalyst according to the present invention, the composition ratio of nickel to cobalt is not particularly limited and may be selected at will. Although the content of rhenium is not particularly limited, it must be determined with the cast of the catalyst taken into consideration because rhenium is more expensive than, cobalt, or molybdenum. Therefore, with regard to the content of rhenium, an atomic ratio of rhenium to, cobalt, of not greater than 0.2, particularly 0.005 to 0.1, may be suitably used.

On the other hand, there is a preferable range of the content of the molybdenum. That is, even the addition of molybdenum in a very small quantity can provide an improvement in activity and selectivity to the hexamethyleneimine, and the effects of its addition are increased and reach a maximum as its quantity added increases. However, when further addition is continued, the molybdenum has an adverse effect on the property of the catalyst until the property becomes poorer than that of a catalyst with no molybdenum added. This is because an excessive addition of molybdenum does not reslt in a greatly negative effect with respect to selectivity, while it results in a remarkably negative effect with respect to activity. The preferred content of molybdenum is such that an atomic ratio of molybdenum to cobalt, is in the range of from 0.001 to 0.1, particularly preferably from 0.005 to 0.08.

Although what configuration the Co, Re, and Mo assume in the catalyst prepared as described above is not always apparent, it is estimated that all of these elements are present in their metallic state and form a solid solution.

2. HYDROGENATION

The reason why the catalytic hydrogenation of ε-caprolactam had no satisfactory success in the prior art is attributable in part to a remarkable poisonous action of the amino acid produced as a by-product on the catalyst and in part to the decomposition of the resulting hexamethyleneimine and the polymerization of the ε-caprolactam under severe reaction conditions. For these reasons, hexamethyleneimine was obtained only in a very low yield. That is, in the case where the hydrogenation reaction is practiced by a conventional batch process, the catalyst is poisoned by the water produced in the reaction and the ε-aminocaproic acid produced by the decomposition of the ε-caprolactam with the water. Although the catalyst of the present invention is highly resistant to such a poison, it is preferred that such materials liable to posion the catalyst are not present. Further, even if th formation of polycaprolactam acan be inhibited to some degree with the use of a suitable solvent, the water produced inevitably causes the formation of polycaprolactam. As can be seen from the foregoing, the water produced in the reaction is an obstacle to the performance of the process of the present invention.

Further, when the hydrogenation reaction is carried out in a conventional batch style, the desired product hexamethyleneimine does not only undergo a further hydrogenation reaction to form a byproduct which leads to a reduction in yield, but also polymerizes itself to form a polymer which is deposited on the catalyst, thereby reducing the hydrogenation activity of the catalyst. Accordingly, it is desirable that the hexamethyleneimine produced in the reaction be removed from the reaction zone as rapidly as possible as it is produced.

WITHDRAWAL OF PRODUCT IN VAPOR PHASE

This problem can be solved by the operational mode of the present invention including withdrawal of the resulting hexamethyleneimine in vapor phase. That is, as a result of various studies for rapidly removing the by-product water and the desired product hexamethyleneimine from the reaction zone, we have found that withdrawal of these materials in a vapor phase together with an excess of a hydrogen gas from the reaction zone was very useful for the process of the present invention.

More specifically, for example, hydrogen gas in excessive amount is blown into the reaction zone to entrain the reaction product therein, and the product entrained in the hydrogen gas is removed from the reaction system and then condensed.

The quantity of the reaction product withdrawn is determined by the quantity of the hydrogen gas supplied. The supply quantity of the hydrogen gas can be selected while the progress state of the reaction is observed. In accordance with this operational mode, the by-product water is distilled together with the hexamethyleneimine, so that the production of an amino acid resulting as a by-product from the hydrolysis of the ε-caprolactum caused by water in the reaction zone is reduced. Accordingly, a catalyst which is not so highly resistant to an acid as the catalyst of the present invention may also be used.

The micromechanism by which outstanding advantages are obtained in the operational mode of the present invention including to withdrawal of the vapor phase of the product may be considered to be as follows. The hydrogenation reaction proceeds on the surface of the solid catalyst, and water is formed with the progress of the reaction. In the case of a batch reaction, because the step in which the water on the surface of the catalyst is dissolved into a solvent surrounding the catalyst is a rate-determining the step, the adverse effect of the water appears on the surface of the catalyst, which makes it impossible to obtain hexamethyleneimine in a high yield. On the other hand, in the case of the vapor phase withdrawal reaction method according to the present invention, because the escape of the produced water from the surface of the catalyst is promoted, the activity of the catalyst is effectively retained, whereby hexamethyleneimine is obtained with a high yield. However, the present invention is not intended to be limited to this concept.

In the case where the product is withdrawn in a vapor phase, the starting material ε-caprolactam and solvent may be charged into the reaction zone by any appropriate method. For example, the raw material ε-caprolactam and solvent may be preliminarily charged into the reaction zone, a mixture of the two materials may be continuously supplied into the reaction zone by means of a pump, or these procedures may be used in combination.

SOLVENT

In general, when the hydrogenation reaction of the ε-caprolactam is carried out, the water formed in the reaction catalyzes the polymerization of the ε-caprolactam to form polycaprolactam, and the reaction in fact proceeds as the hydrogenation reaction of the polycaprolactam which results in a remarkable reduction in the rate of the desired reaction. Therefore, in practicing the hydrogenation reaction of the ε- caprolactam, a suitable solvent is preferably used. The solvent usable for the hydrogenation reaction of the ε-caprolactam may be any solvent inert to the hydrogenation reaction,.

Examples of such a solvent are: cyclic ethers such as dioxane, morpholine and the like; diethylene glycol alkyl ethers such as dithylene glycol monomethyl ether, diethylene glycol monoethyl ether, diethylene glycol dimethyl ether, diethylene glycol diethyl ether and the like; glycerine alkyl ethers such as glycerine trimethyl ether and the like; straight chain or cyclic saturated hydrocarbons such as cyclohexane, trimethyl cyclohexane, monane, decane, cyclodecane, dodecane, cyclodedecane, decalin and the like; and tertiary amines such as tri-n-butyl amine and the like. Particularly when dioxane or diethylene glycol dialkyl ether is used, a high yield of hexamethyleneimine can be obtained.

In adopting the operational mode including the vapor phase withdrawl of the product, these solvents which have a boiling point higher than 138° C, which is the boiling point of the objective hexamethyleneimine, and lower than 250° C among the above-mentioned solvents inert to the hydrogenation reaction are preferable. This is because a solvent having a higher boiling point is difficult to withdraw in the form of a vapor phase from the reaction zone. Also, the solvent preferably has a higher boiling point than that of the hexamethyleneimine. With a lower boiling point, the solvent is easier to withdraw as a vapor phase than the product hexamethyleneimine and the hexamethyleneimine accumulates in the reaction zone, which causes polymerization or undesirable successive reactions.

Among these solvents, typical solvents are straight chain or cyclic saturated hydrocarbons having from 9 to 14 carbon atoms and mixtures of these hydrocarbons. For reasons of availability and economy as an industrial product, decalin and saturated hydrocarbon mixtures are particularly preferred. The quantity of the solvent used is not particularly limited, but the solvent is preferably used in quantities of 3 to 20 times that of the starting material.

The temperature and pressure at which the hydrogenation raction is carried out vary, depending upon the catalyst used and its quantity. Ordinarily, the reaction temperature is in the range of 100 to 350° C, preferably 150° to 300° C. Although the reaction pressure is not particularly limited, a pressure of from atmospheric pressure to 500 atmospheres is generally used. However, in the practice of the operational mode including the vapor phase withdrawal of the product, the reaction pressure is in the range of from atmospheric pressure to 200 kg/cm$^2$.G, preferably from 5 to 100 kg/cm$^2$.G.

Hereinafter, the present invention will be set forth in more detail with reference to the specific examples. However, the present invention is in no way to be limited by these examples unless the invention oversteps the subject matter thereof.

EXAMPLE-1

An aqueous solution containing 240 g of ammonium bicarbonate ($NH_4HCO_3$) in 1200 g of distilled water is dropped into an aqueous solution containing 300g of cobalt nitrate (Co ($NO_3$)$_2$.6$H_2O$) in 240g of distilled water with stirring, whereby a purple-red precipitate of basic cobalt carbonate is formed. The precipitate is separated by filtration, and then washed with distilled water to provide a basic cobalt carbonate cake. The cobalt content of this cake was 12.5% by weight. An aqueous solution containing 0.363 g of rhenium heptoxide ($Re_2O_7$) and 4.57 g of ammonium molybdate ( ($NH_4$)$_6Mo_7O_{24}$ . 4$H_2O$ ) in 150 g of distilled water is added to 23.6 g of the cake, which is thoroughly mixed and kneaded, and then 5.90 g of powdery zirconium oxide ($ZnO_2$) which has been calcined for two hours at 900° C in the air is added thereto. The resulting slurry is mixed, kneaded, and dried with heating at about 80° C, and thereafter dried at 80°-120° C for 12 hours. The powder thus obtained is heated up to 270° C in an air stream having a flow rate of about 250 cc/min over about 2 hours, maintained at 270° C for 30 minutes, and then heated further to 450° C over about 15 minutes. After the air stream has been replaced by a stream of an inert gas such as nitrogen, a hydrogen stream having a flow rate of 1,000 cc/min is introduced in place of the inert gas stream. Said powder is maintained at 450° C for 3 hours and then cooled to an ordinary temperature, whereafter the hydrogen stream is replaced by a nitrogen stream. Then, air is introduced gradually lest the catalyst temperature should exceed 50° C until the catalyst will not generate heat even in an only air stream, when the powder is taken out therefrom and stored in a sealed container. Thus a Co-Re-Mo-$ZrO_2$ catalyst (catalyst - 1) is obtained.

1 g of this Catalyst-1 and 10 g of ε-carprolactam were fed together with 30 ml of diethylene glycol diethyl ether as a solvent to a 100 ml autoclave provided with an electromagnetic agitator, and contacted with hydrogen to cause a reaction under a pressure of 80 atm and at a temperature of 250° C for one hour while the agitation speed was maintained at 1000 r.p.m. After the reaction had been completed, the reaction product was separated from the catalyst and subjected to gas chromatography in accordance with an internal standard method.

The results obtained are shown in Table 1.

EXAMPLES-2 & 3

Reactions were carried out under the same conditions as those in Example-1 in the presence of a catalyst obtained in the same manner as Catalyst-1 except that the amount of ammonium molybdate used was controlled so that the atomic ratio of molybdenum to cobalt (Mo/Co) might be 0.050 (Catalyst-2) and 0.025 (Catalyst-3), respectively. The reaction results obtained are shown in Table 1.

EXAMPLES-4 & 5

Catalysts-4 and 5 were prepared in the same manner as Catalyst-1 except that no zirconium oxide was employed in either catalyst and that the amounts of rhenium heptoxide and ammonium molybdate added were controlled so that the atomic ratio of rhenium to cobalt (Re/Co) might be 0.06 while the atomic ratio of molybdenum to cobalt (Mo/Co) might be 0.030 (Catalyst-4) and 0.015 (Catalyst-5), respectively.

The results obtained under the same reaction conditions as those in Example-1 with respect to each of the catalysts thus prepared are shown in Table 1.

EXAMPLES-6 & 7

Catalysts-6 and 7 were prepared in the same manner as Catalyst-1 except that no zirconium oxide was added in either catalyst and that the amount of ammonium molybdate added was controlled so that the atomic ratio of molybdenum to cobalt (Mo/Co) might be 0.030 (Catalyst-6) and 0.015 (Catalyst-7), respectively.

The results obtained under the same reaction conditions as those in Example-1 with respect to each of the catalysts thus prepared are shown in Table 1.

EXAMPLES-8, 9 & 10, and Comparative Example-1

Catalysts-8 through 10 were prepared in the same manner as Catalyst-1 except that no zirconium oxide and rhenium were added in any of the catalysts and that the amount of ammonium molybdate added was controlled so that the atomic ratio of molybdenum to cobalt (Mo/Co) might be 0.050 (Catalyst-8), 0.030 (Catalyst-9), 0.013 (Catalyst-10) and 0 (Catalyst-A), respectively.

The results obtained under the same reaction conditions as those in Example-1 with respect to each of the catalysts thus prepared are shown in Table 1.

Table 1

| Example No. | Catalyst No. | Catalyst Composition | ZrO₂/Co Weight Ratio | Re/Co Atomic Ratio | Mo/Co Atomic Ratio | Reaction Results (Mole %) ε-Caprolactam Conversion Ratio | Hexamethyleneimine yield |
|---|---|---|---|---|---|---|---|
| 1 | 1 | Co-Re-Mo-ZrO₂ | 2 | 0.03 | 0.075 | 43 | 17 |
| 2 | 2 | '' | 2 | 0.03 | 0.050 | 64 | 27 |
| 3 | 3 | '' | 2 | 0.03 | 0.025 | 62 | 28 |
| 4 | 4 | Co-Re-Mo | 0 | 0.06 | 0.030 | 95 | 31 |
| 5 | 5 | '' | 0 | 0.06 | 0.015 | 87 | 38 |
| 6 | 6 | '' | 0 | 0.03 | 0.030 | 84 | 35 |
| 7 | 7 | '' | 0 | 0.03 | 0.015 | 92 | 32 |
| 8 | 8 | Co-Mo | 0 | 0 | 0.050 | 57 | 20 |
| 9 | 9 | '' | 0 | 0 | 0.030 | 67 | 14 |
| 10 | 10 | '' | 0 | 0 | 0.013 | 66 | 17 |
| Comparative Example 1 | A | Co | 0 | 0 | 0 | 62 | 13 |

EXAMPLE-11

Catalyst-11 was obtained by the same process for the preparation of the catalyst described in Example-1 wherein nickel nitrate (Ni (NO₃)₂. 6H₂O) was used in place of cobalt nitrate and alumina silica (SA) (Al₂O₃·SiO₂) in place of zirconium oxide, while rhenium heptoxide was added in such an amount that the atomic ratio of rhenium to nickel (Re/Ni) would be 0.03 and ammonium molybdate in such an amount that the atomic ratio of molybdenum to nickel (Mo/Ni) would be 0.075.

The results obtained under the same conditions as those in Example-1 except that the reaction pressure was 120 atm are shown in Table 2.

EXAMPLE-12

11.8 g of the basic cobalt carbonate cake containing 12.5% by weight cobalt which was used in the preparation of Catalyst-1, and 12.3 g of the basic nickel carbonate cake containing 12.2% by weight nickel which was used in the preparation of Catalyst-15 are thoroughly mixed and kneaded to which an aqueous solution containing 0.363 g of rhenium heptoxide (Re₂O₇) and 0.914 g of ammonium molybdate ( (NH₄)₆Mo₇O₂₄.4H₂O) in 150 g of distilled water is added. The mixture is mixed, kneaded, and dried with heating at about 80° C, and thereafter dried at 80°-120° C for 12 more hours. The powder thus obtained was decomposed, reduced, and stabilized in the same manner as Catalyst-1 to provide Catalyst-12.

The results obtained under the same reaction conditions as those in Example-1 are shown in Table 2.

EXAMPLE-13

Catalyst-13 was prepared in the same manner as Catalyst-12 except that no rhenium was added and that the atomic ratio of molybdenum to cobalt and nickel (Mo/Co + Ni) was 0.03.

A reaction was carried out in the presence of Catalyst-13 under the same conditions as those in Example-1, resulting in 39 mole % of the ε-caprolactam conversion ratio and 13 mole % of the hexamethyleneimine yield.

EXAMPLE-14 & Comparative Example-2

Catalyst-14 was prepared in accordance with the process for the preparation of Catalyst-1 using nickel nitrate and ammonium molybdate in such an amount that the atomic ratio of molybdanum to nickel (Mo/Ni) would be 0.03 without addition of rhenium and zirconium oxide.

Catalyst-B was prepared in the same manner as Catalyst-14 without adding molybdenum but using only nickel nitrate.

The results obtained under the same reaction conditions as those in Example-1 with respect to each of the catalysts are shown in Table 2.

Table 2

| Example No. | Catalyst No. | Catalyst Composition | Al₂O₃SiO₂ Ni Weight Ratio | Co/Ni Atomic Ratio | Atomic Ratio of Re/Ni or Re/Ni + Co | Atomic Ratio of Mo/Ni or Mo/Ni + Co | Reaction Results (Mole %) ε-Caprolactam Conversion Ratio | Hexamethyleneimine Yield |
|---|---|---|---|---|---|---|---|---|
| 11 | 11 | Ni-Re-Mo-S A | 2 | 0 | 0.03 | 0.075 | 47 | 14 |
| 12 | 12 | Ni-Co-Re-Mo | 0 | 1 | 0.03 | 0.015 | 52 | 9 |
| 13 | 13 | Ni-Co-Mo | 0 | 1 | 0 | 0.03 | 39 | 13 |
| 14 | 14 | Ni-Mo | 0 | 0 | 0 | 0.03 | 27 | 9 |
| Comparative Example-2 | B | Ni | 0 | 0 | 0 | | 1 | Trace |

EXAMPLE—15

Table 3 shows the results obtained in the initial period of about 100 hours of a long run carried out in a reactor of the continuous vapor phase withdrawal type using Catalyst-2 (composition: Co-Re-Mo-ZrO₂) and diethylene glycol diethyl ether as a solvent.

The reactor of the continuous vapor phase withdrawal type consists of a 2 l autoclave provided with an electromagnetic agitator; a starting material feed means principally consisting of a feed pump; a solvent feed means; a hydrogen feed means; a vapor phase withdrawal means with a condenser; a liquid phase withdrawal means with a sintered metal filter; and a level gage. Hydrogen having a pressure of is passed through the reactor at a flow rate of 1500Nl/h., and a low boiler produced by the reaction and mainly consisting of water and hexamethyleneimine which are likely to form a cause for deterioration of a catalyst is withdrawn out of the reactor together with a part of the solvent through the vapor phase withdrawal means. The liquefiable constituents in the effluent thus withdrawn are liquefied in the condenser and recovered with a gas.

The concentration of the starting material and the total amount of the liquid in the reactor in motion are maintained at a predetermined level by operation of the starting material feed means, solvent feed means, and hydrogen feed means in accordance with the results of the analysis of the liquid in the reactor drawn through the liquid phase withdrawal means and with the indication of the level gage. The reaction velocity is controlled by the reaction temperature.

The yield of hexamethyleneimine was 85 mole % even after 900 hours of a continuous reaction, demonstrating that a further continuation of the run was possible.

The reaction conditions were as follows:

The reaction temperature was 210° C, pressure 120 atm, amount of the catalyst fed 30 g, and the solvent was diethylene glycol diethyl ether, the amount of the liquid in the reactor being maintained at about 1000 ml, and the concentration of the $\epsilon$-caprolactam in the reactor being maintained at from 5 to 10% by weight. The amount of hexamethyleneimine obtained was 20 g/h.

Table 3

| Ex. No. | Catalyst No. | Catalyst Composition | Reaction Period (h) | Hexamethyleneimine Yield (Mole %) | High Boiler (Mole %) |
|---|---|---|---|---|---|
| 15 | 2 | Co-Re-Mo-ZrO$_2$ | 101 | 73 | 6 |

EXAMPLES-16 through 19

Reactions were carried out under the same conditions as those in Example-1 except that Catalyst-11 (composition: Ni-Re-Mo-SiO$_2$. Al$_2$O$_3$) and various solvents were used and that a pressure of 120 atm and various reaction periods were employed.

The results as well as the reaction conditions employed are shown in Table 4.

Table 4

| Example No. | Reaction Period (h) | Solvent | $\epsilon$-Caprolactam Conversion Ratio | Hexamethyleneimine Yield |
|---|---|---|---|---|
| 16 | 6 | dioxane | 38 | 17 |
| 17 | 2 | diethylene glycol dimethyl ether | 62 | 10 |
| 18 | 6 | cyclohexane | 99 | 4 |
| 19 | 2 | diisoamyl ether | 39 | 10 |

EXAMPLES-20 THROUGH 25

Reactions were carried out under the same conditions as those in Example -1 except that Catalyst-1 (composition: Co-Re-Mo-ZrO$_2$) and various solvents were used and that the reactions were effected for 2 hours utilizing 5 g of $\epsilon$-caprolactam.

The reaction results are shown in Table 5 below.

Table 5

| Example No. | Solvent | $\epsilon$-Caprolactam Conversion Ratio | Hexamethyleneimine Yield |
|---|---|---|---|
| 20 | dioxane | 85 | 34 |
| 21 | diethylene glycol dimethyl ether | 67 | 26 |
| 22 | diethylene glycol diethyl ether | 42 | 30 |
| 23 | morpholine | 52 | 9 |
| 24 | tri-n-butylamine | 82 | 15 |
| 25 | diethylene glycol monoethyl ether | 50 | 7 |

EXAMPLE—26

3.0 g of Catalyst-1 (composition: Co-Re-Mo-ZrO$_2$), 30.0 g of $\epsilon$-caprolactam as a starting material, and 150 g of diethylene glycol diethyl ether as a solvent are fed to a 300 cc autoclave provided with a vapor phase withdrawal means, and hydrogen is blown into a reaction zone at a flow rate of 960 Nl/t, wherein the reaction temperature is maintained at 230° C while the hydrogen pressure at 80 kg/cm$^2$.G. The solvent and the reaction product withdrawn in a vapor phase are condensed in a condenser. The condensate was withdrawn at 30-minute intervals, a small amount of n-propanol was added thereto, and the solution was homogenized which was then subjected to quantitative analysis by gas chromatography.

The yield of hexamethyleneimine was 66 mole % after a 3-hour period, And 92 mole % after a 5-hour period, respectively.

EXAMPLE—27A

Withdrawal of Product in Vapor Phase 3.0 g of a catalyst prepared from cobalt nitrate, rhenium heptoxide, and ammonium molybdate as starting materials and principally consisting of Co in such an amount that the atomic ratio of Re/Co equals 0.03 and of Mo/Co equals 0.075, said catalyst using ZrO$_2$ as a carrier in such an amount that the atomic ratio of Co/ZrO$_2$ equals 0.5, 30.0 g of $\epsilon$-caprolactam as a starting material, and 150 g of decalin as a solvent were fed to a 300 cc autoclave provided with a vapor phase withdrawal means, and hydrogan was blown into a reaction zone at a flow rate of 960 Nl/h, wherein the reaction temperature was maintained at 230° C while the hydrogen pressure at 80 Kg/cm$^2$.G. The solvent and the reaction product withdrawn in a vapor phase were condensed in a condenser. The condensate was withdrawn at 30-minute intervals, a small amount of n-propanol was added thereto, and the solution was homogenized which was then subjected to quantitative analysis by gas chromatography.

The yields of hexmethyleneimine (HMI) on ε-caprolactam fed obtained 3, 4 and 5 hours after the hydrogen gas was passed through the reactor were as follows:

| Elapsed Reaction Time | HMI Yield |
|---|---|
| 3 Hours | 65 Mole % |
| 4 Hours | 84 Mole % |
| 5 Hours | 86 Mole % |

EXAMPLE—27B

Without Withdrawal of Product 1.0 g of the catalyst used in Example 27A, 5.0 g of ε-caprolactam, and 30 g of decalin as a solvent were fed to a 100 cc autoclave provided with an agitator, and a reaction was carried out by a batch process of 3- and 5-hour periods, wherein the reaction temperature was maintained at 230° C while the hydrogen pressure at 80 kg/cm$^2$.G. The reaction product was liquified and subjected to quantitative analysis as in Example-1. The reaction results were as follows:

| Reaction Period | HMI Yield |
|---|---|
| 3 Hours | 30 Mole % |
| 5 Hours | 27 Mole % |

EXAMPLE—28

The reaction results obtained under the same conditions as those in Example-27A except that the hydrogen pressure was maintained at 20 kg/cm$^2$.G. were as follows:

| Reaction Period | HMI Yield |
|---|---|
| 3 Hours | 40 Mole % |
| 6 Hours | 83 Mole % |

EXAMPLE—29

3 g of the same catalyst as was employed in Example-27A, 30 g of ε-caprolactam, and 150 ml of n-decane as a solvent were fed to an autoclave provided with a withdrawal means, and hydrogen was blown into a reaction zone at a flow rate of 960 Nl/h, wherein the reaction temperature was maintained at 230° C while the hydrogen pressure at 80 kg/cm$^2$.G.

The solvent and the reaction product withdrawn in a vapor phase were condensed in a condenser. The yields obtained after 2 and 3 hours were as follows:

| Reaction Period | HMI Yield |
|---|---|
| 2 Hours | 40 Mole % |
| 3 Hours | 86 Mole % |

EXAMPLE—30

The reaction results obtained under the same conditions as those in Example-2 except that 150 ml of cyclodecane was used as a solvent were as follows:

| Reaction Period | HMI Yield |
|---|---|
| 2 Hours | 35 Mole % |
| 4 Hours | 84 Mole % |

EXAMPLE—31

Table 6 shows the results obtained under the same reaction conditions as those in Example-15 except for the following conditions:
  Catalyst: Catalyst-4 (composition: Co-Re-Mo)
  Amount of Catalyst Fed: 10 g
  Solvent: Normal Paraffin (mixture of normal paraffins having 12, 13, and 14 carbon atoms, respectively)
  Reaction Temperature: 200°–220° C
  Reaction Pressure: 20 atm Table 6

| Ex. No. | Catalyst No. | Catalyst Composition | Reaction Period (h) | Hexamethyleneimine Yield (Mole %) | High Boiler Yield (Mole %) |
|---|---|---|---|---|---|
| 32 | 4 | Co-Re-Mo | 843 | 86 | 4 |

The amount of hexamethyleneimine obtained was 20 g/h as in Example-15.

The yield of hexamethyleneimine was 85 mole % even after 2500 hours of a continuous reaction, demonstrting that a further continuation of the run was possible.

EXAMPLE—32

1.0 g of Catalyst-4 of Example-4 (composition: Co-Re-Mo), 30.0 g of ε-caprolactam as a starting material and 150 ml of normal dodecane as a solvent are fed to an autoclave (with a capacity of 300 ml) provided with an electromagnetic agitator, an inlet for ejecting hydrogen into a vapor phase, and a vapor phase withdrawal outlet with a condenser, and the reaction temperature is maintained at 210° C, reaction pressure at 15 atm, hydrogen flow rate at 200 l/h, and agitation speed at 1000 r.p.m., whereupon the materials in the autoclave except the catalyst (unreacted ε-caprolactam, the solvent, and the reaction product) come out through the vapor phase withdrawal outlet together with hydrogen over about 2 hours. The resulting products were cooled and separated into a gas and liquids. On the analysis by means of gas chromatography of the liquids thus separated, it was found that the conversion ratio of ε-caprolactam fed was 92 mole %, and that 94 mole % of the converted ε-caprolactam was hexamethyleneimine. The liquids obtained also contained a small amount of normal hexylamine and a high boiler.

What is claimed is:
1. A process for producing hexamethyleneimine by the catalytic hydrogenation of ε-caprolactam in the liquid phase which comprises contacting ε-caprolactam with hydrogen over a catalytic amount of a hydrogenation catalyst selected from the group consisting of: a) essentially cobalt-molybdenum and having an atomic ratio range of molybdenum/cobalt of 0.1 to 0.001/1.0; b) essentially cobatl-rhenium-molybdenum having an atomic ratio of molybdenum/cobalt and of rhenium/cobalt from 0.001 to 0.1 and up to 0.2/1.10 respectively, suspended in a solvent inert to the hydrogenation reaction at a temperature of from 100° to 350° C and under a hydrogen pressure ranging from atmospheric pressure to 200 kg/cm$^2$, thereby to cause the catalytic hydrogenation.

2. The process according to claim 1 wherein the catalysts contains molybdenum in an atomic ratios of Mo/Co of 0.005 to 0.08.

3. The process according to claim 1 wherein the catalyst contains rhenium in an atomic ratio of Re/Co of from 0.005 to 0.1.

4. The process according to claim 1 wherein said liquid phase comprises a solvent and the solvent is selected from the group consisting of dioxane, diethylene glycol alkyl ethers, and straight and cyclic saturated hydrocarbons having from 9 to 14 carbon atoms, and mixtures thereof.

5. The process according to claim 4 wherein said diethylene glycol alkyl ether is selected from the group consisting of diethylene glycol monoalkyl ethers and diethylene glycol dialkyl ethers wherein the alkyl is selected from methyl and ethyl.

6. The process according to claim 1 wherein the reaction product is withdrawn in the vapor phase from the reaction zone.

7. The process according to claim 6 wherein the ε-caprolactam and hydrogen are continually fed to the reaction zone.

8. The process according to claim 7 wherein during the hydrogenation reaction, an excessive quantity of hydrogen gas is blown into the reaction zone, and the reaction product is entrained in the hydrogen gas to remove said reaction product from the reaction zone and to then condense the reaction product.

9. the process according to claim 7 wherein the liquid phase comprises a solvent and the solvent is selected from the group consisting of straight chain and cyclic saturated hydrocarbons having from 9 to 14 carbon atoms and mixtures thereof.

10. The process according to claim 9 wherein said hydrocarbon is selected from the group consisting of n-nonane, n-decane, n-dodecane, decalin, cyclodecane, cyclododecane, and trimethyl cyclohexane.

11. The process according to claim 9 wherein said hydrocarbon is selected from the group consisting of decalin, n-decane, cyclodecane, and n-dodecane.

12. The process according to claim 9 wherein said hydrocarbon is decalin.

* * * * *